United States Patent [19]

Hwu et al.

[11] Patent Number: 5,013,862

[45] Date of Patent: May 7, 1991

[54] PROSTANOIDS AND SYNTHESIS THEREOF

[75] Inventors: Jih R. Hwu; Jeffrey A. Robl, both of Baltimore, Md.

[73] Assignee: The Johns Hopkins University, Baltimore, Md.

[21] Appl. No.: 360,086

[22] Filed: Jun. 1, 1989

Related U.S. Application Data

[62] Division of Ser. No. 44,322, Apr. 30, 1987, Pat. No. 4,855,437.

[51] Int. Cl.$^5$ .............................................. C07C 251/00
[52] U.S. Cl. ....................................................... 560/60
[58] Field of Search ........................................... 560/60

[56] References Cited

U.S. PATENT DOCUMENTS 4,112,224 9/1978 Bundy .................................. 542/426
4,275,213 6/1981 Bundy .................................. 548/240

OTHER PUBLICATIONS

Padwa, J. Org. Chem. Sl 3125 (1986).

*Primary Examiner*—Robert Gerstl
*Attorney, Agent, or Firm*—Cushman, Darby & Cushman

[57] ABSTRACT

Prostaglandin analogues which include a bicyclic isoxazolidine nucleus are disclosed. These analogues may be used to prepare other prostaglandins. Essential to the synthesis is intramolecular nitrone-alkene cycloaddition involving an alkenyl nitrone in which the reacting centers are separated by two carbons.

1 Claim, 2 Drawing Sheets

PROSTANOIDS AND SYNTHESIS THEREOF

This is a division of Application No. 07/044,322, filed Apr. 30, 1987 now U.S. Pat. No. 4,355,437.

The present invention relates to prostaglandin analogues and their preparation. The invention is also concerned with certain novel intermediates which are useful in the preparation of prostaglandins.

The work referred to herein was supported in part by grants from the Department of Health and Human Services and the National Science Foundation.

BACKGROUND OF THE INVENTION

Prostaglandins (PGs) are attractive targets for improved synthesis due to their structural complexity and their known pharmacological activities. Extensive research efforts have been directed towards prostaglandins and their preparation as is evident from the many patents and publications relative thereto. See in this regard S.M.F. Lai and P.W. Manley, Nat. Prod. Rep., 1984, 409; 'New Synthetic Routes to Prostaglandins and Thromboxanes,' eds. S. M. Roberts and F. Scheinmann, Academic Press, New York, 1982; K. C. Nicolaou, G. P. Gasic, and W. F. Barnette, Angew. Chem., Int. Ed. Engl., 1978, 17, 293; J. S. Bindra and R. Bindra, 'Prostaglandin Synthesis', Academic Press, New York, 1977; "Prostaglandin Research", ed. P. Crabbe, Academic Press, New York, 1977.

Generally speaking, prior procedures for preparing prostaglandins have suffered from the fact that a great number of highly complex procedural steps are needed in order to obtain the ultimately desired products. An important object of the present invention is to provide simplified procedures for obtaining prostaglandins. Other objects will also be hereinafter apparent.

BROAD DESCRIPTION OF THE INVENTION

One important aspect of the invention is the provision of prostaglandin H (PGH) analogues which have a bicyclic isoxazolidine nucleus. This feature of the invention is based on the finding that intramolecular nitrone-alkene cycloaddition involving a C-alkenyl nitrone is possible to construct the basic nucleus of prostaglandin H analogues. The C-alkenyl nitrones used herein are such that the reacting centers are separated by two carbon atoms. The intramolecular nitrone-alkene cycloaddition of such a nitrone functions to form the bicyclic isoxazolidine which, as noted, provides the nucleus desired for PGH analogues. The invention thus offers a highly convenient way of preparing PG analogues directly from appropriate acyclic precursors. Furthermore, the bicyclic isoxazolidines or PGH analogues so prepared can be used to form other PGs and their analogues as described later herein.

The PGH analogues which are characterized by a bicyclic isoxazolidine nucleus according to the invention is structurally represented as follows:

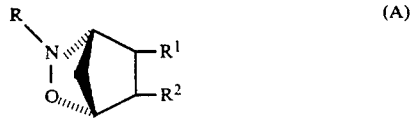

when R is hydrogen or optionally substituted alkyl, aryl or aralkyl, and R¹ and R² each represent, in whole or part, atoms necessary to complete a prostaglandin structure. Thus, for example, R¹ may represent the group

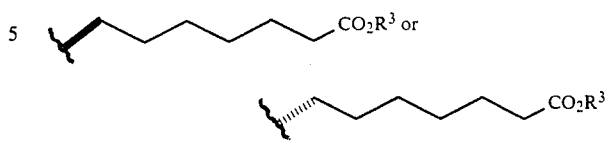

where R³ is hydrogen or lower alkyl; and R² may stand for

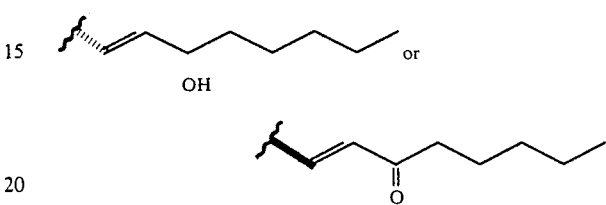

or a fragment thereof.

As possibly a simpler structural designation, the bicyclic isoxazolidines may also be shown as follows:

where R has the meaning given above and X represents an optionally substituted two carbon linking group characteristic of a PG structure.

As indicated, the bicyclic isoxazolidines are prepared, according to the invention, by intramolecular nitrone-alkene cycloaddition of C-alkenyl nitrones. This may be accomplished by thermolysis of the alkenyl nitrones which, for present purposes, may be structurally illustrated as follows:

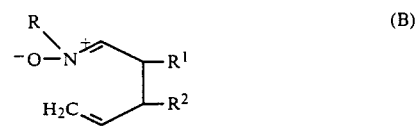

where R, R¹ and R² have the meaning given above.

As examples of R, there may be mentioned alkyl of up to 8 carbons or more, e.g. methyl, ethyl, propyl, butyl or the like, phenyl, naphthyl, tolyl, benzyl, phenethyl. The R¹ and R² substituents may be widely varied and can include simple or complex substituants as indicated above.

The nitrone-alkene (B) is usefully prepared by reacting a substituted hydroxylamine RNHOH with an appropriate γ, δ-aldehyde of the formula O=CH—X—CH=CH₂.

The various features of the invention are more specifically illustrated by reference to the following examples and accompanying drawings wherein:

FIG. 1 illustrates generally how the PGH analogues (A) of the invention may be converted to other PGs;

FIG. 2 sets out a reaction scheme based on a model study to show how the PGH analogues of the invention may be prepared and converted to other prostaglandin analogues; and FIG. 3 illustrates the preparation of specific PGH analogues.

DETAILED DESCRIPTION OF THE INVENTION

Figure 1:
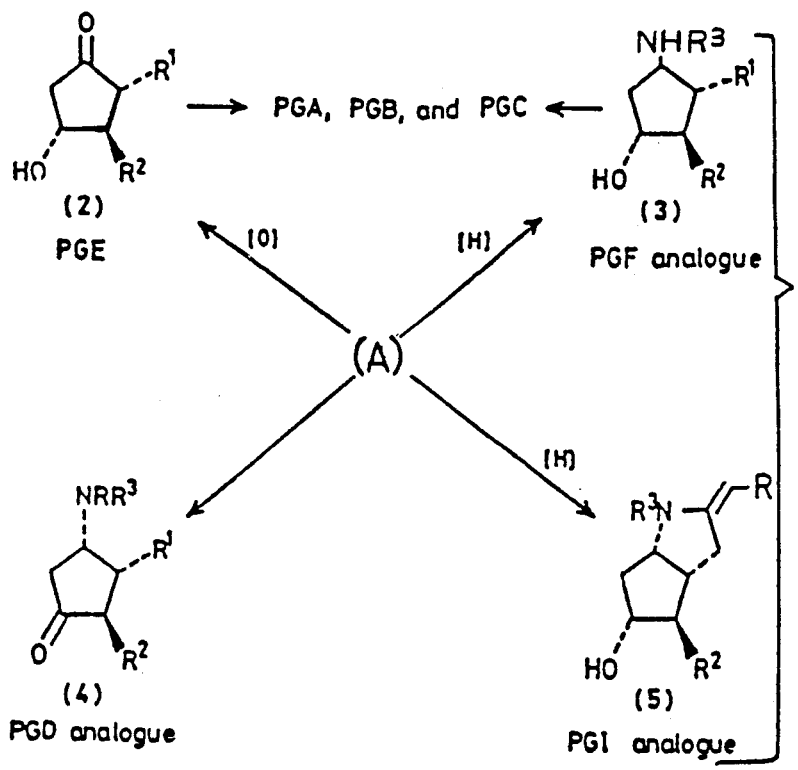

As shown in FIG. 1, the PGH analogues (A) characterized by the bicyclic isoxazolidine nucleus may be used to prepare various types of known prostaglandins or their analogues by oxidation (O) or hydrogenation (H). It will be appreciated that the various R, $R^1$-$R^3$ substituents shown in FIG. 1 can be varied and will be chosen to prepare the desired PG, the compound (A) being used to provide a nucleus which is essential to the various prostaglandins.

Figure 2:
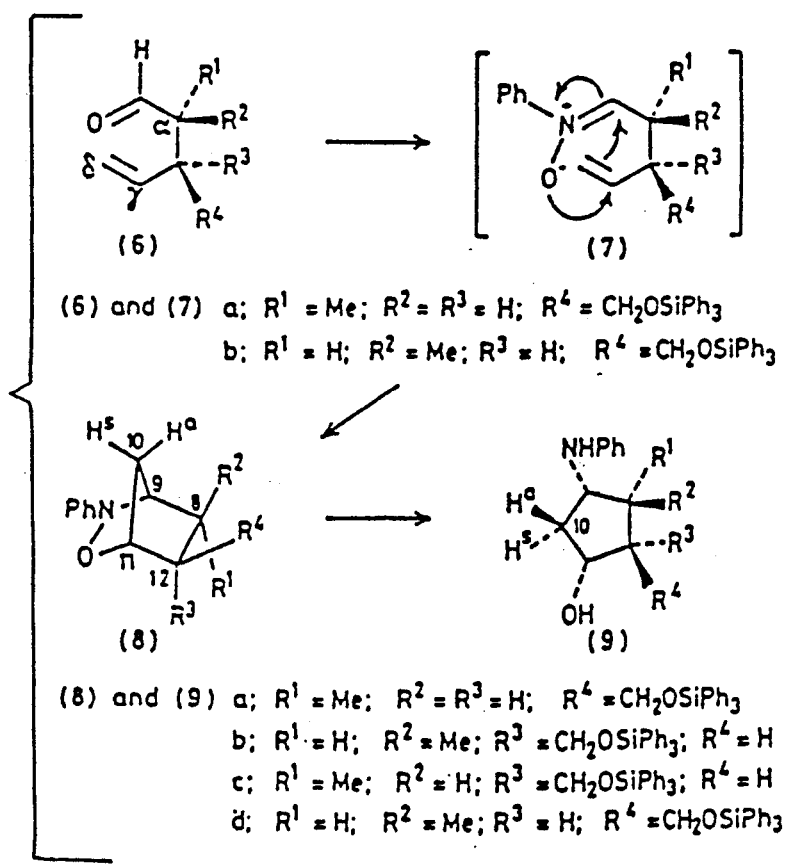

With reference to FIG. 2, which illustrates a model study representative of the reactions involved in carrying out the various process features of the invention, it will be noted that a γ,δ-unsaturated aldehyde (6) and an N-substituted hydroxylamine, e.g., phenylhydroxylamine, both readily available or obtainable materials, are reacted to give a nitrone (7) which is then converted by intramolecular nitrone-alkene cycloaddition to form the bicyclic isoxazolidine (8). The latter can then be used as an intermediate in the production of PGA, PGB, etc. as shown in FIG. 1.

As in the case of the FIG. 1 illustration, the various R, $R^1$-$R^4$ substituents referred to in FIG. 2 are representative only and are not intended to limit the invention. In particular, the invention contemplates broadly the conversion of an alkenyl aldehyde, notably a γ,δ-unsaturated aldehyde, by reaction with a hydroxylamine to give the corresponding alkene nitrone which is then bicyclized to the desired bicyclic isoxazolidine. This latter reaction, as noted earlier, is fundamental to the invention and of broad application. Thus, the only limitation on substituents in the reactants involved is that they are such as not to undesirably affect the orientation of the addition of the nitrone moiety to the C=C double bond in the formation of the bicyclic isoxazolidine.

The conditions used in carrying out the indicated reactions, e.g., temperature, time, solvents, etc. can be widely varied except as otherwise indicated herein. Typically the reaction between the alkenyl aldehyde and the hydroxylamine, and the cycloaddition of the resulting nitrone, are carried out by mixing the aldehyde and hydroxylamine together at any desired temperature, e.g. room temperature, the cycloaddition then being accomplished by heating at 80°-170° C. for 3 minutes to 48 hours. Any convenient inert solvent can be employed for this purpose such as benzene, toluene, halobenzenes, etc.

A wide variety of N-substituted hydroxylamines may be used, for example, N-alkyl- or N-aryl-hydroxylamines such as N-methylhydroxylamine, N-phenylhydroxylamine or the like. It is also contemplated that silyated derivatives of the N- c substituted hydroxylamines can be used.

The following examples further illustrate the invention.

Example 1

This example makes reference to the reactions shown in FIG. 2. Aldehyde starting material was prepared using the following reaction scheme:

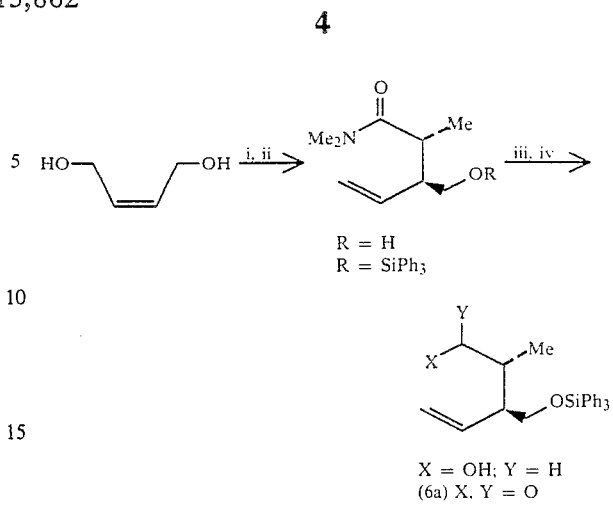

The dihydroxy compound starting material was reacted (i) with $EtC(OMe)_2NMe_2$ (2 equivalents) in xylene by refluxing for 18 hours. The product (in 70% yield) was then (ii) reacted with 2.0 equivalents of $Ph_3SiCl$ in pyridine at 0° C. for 30 minutes (99% yield). This product was reacted (iii) with $LiBHEt_3$ (2.4 equivalents) in tetrahydrofuran at −5° C. for 24 hours followed by (iv) oxidation involving $CrO_3.2$ pyridine (6.0 equivalents) in $CH_2Cl_2$ at room temperature (25° C.) for 45 minutes. The diastereoisomeric purity of the resulting aldehyde 6(a), as determined by NMR spectroscopy, was found to be equal to or greater than 94%. A minor amount of 6(b), resulting from epimerization of 6(a), was also present but could not be separated from 6(a) by chromatographic techniques.

A mixture of aldehyde (6a) [containing 5% of isomer [6b)] and molecular sieves (type 5A) in chlorobenzene was stirred at −6° C. while N-phenyl hydroxylamine (12 equivalents) was added over a two-hour period. The resulting solution was stirred for an additional 45 min., and then gently refluxed for 25 min. Subsequent workup afforded in 64% yield (8a) and (8b) in a ratio of 1:1, plus 3% of 8(c) arising from 6(b). The remaining adduct (8d), desired for spectroscopic purposes, could be obtained in low yields under the same reaction conditions when a mixture of (6a) and (6b) obtained by epimerization of (6a) in the ratio of 60:40 was used.

A detailed $^1H$ n.m.r. study was performed on all of the bicyclic isoxazolidines (8a–d). Initial assignments of the aliphatic protons were made by the use of homonuclear correlated 2-dimensional n.m.r. spectroscopy (COSY). Coupling constants were obtained by extensive double irradiation experiments of protons in the 1-dimensional n.m.r. spectrum. The important observations are as follows: (i) W coupling between $H^{10s}$ and $H^8$ indicated that $H^8$ was in the endo position. Likewise, W coupling between $H^{10s}$ and $H^{12}$ indicated that $H^{12}$ was also in the endo position. (ii) Of great importance were the values of $J_{8,9}$ and $J_{11,12}$ A small value for $J_{8,9}$ (<1.0 Hz) indicated that $H_8$ was in the endo position. The same was true for the values of $J_{11,12}$. In all cases, $J_{8-exo,9}$ was found to have values in or near the expected range of 3.0-4.0 Hz[5,] while $J^{11,12-exo}$ was usually lower in value (1.6 Hz). (iii) Coupling constant $J_{8,12}$ was also of importance. A larger coupling constant (≅6.0 Hz) indicated a cis relationship between the protons whereas a smaller value (≅5.5 Hz) indicated a trans relationship.

To assist in the assignment of structures and to show that the method can be used for the synthesis of PGF analogues (3), these compounds were reduced (H$_2$, Pd/C) to give the corresponding amino alcohols (9a-d). Thus, (8a) and (8b) were converted to (9a) (81%) and (9b) (92%), respectively, in 9 hours. However, (8c) was reduced to (9c) in only 53% yield after 50 hours (24% of the starting material was recovered). Furthermore, (8d) gave (9d) in 90% yield in only 1.5 hours. These relative reaction rates correlated well with the expected reductive activity of compounds (8a-d) based on the influence of steric hindrance on the metal catalysed hydrogenation.

The foregoing example based on the indicated model study illustrates how the invention provides a unique and efficient synthetic method to construct the nuclei of PGH and PGF analogues, i.e., (A) and (3). In this model study, enal (6a) was significant epimerization at the α-carbon in (6a). The formation of (8) is based on an intramolecular nitrone-alkene cycloaddition involving C-alkenyl nitrones in which the reacting centers are separated by two carbon atoms. By appropriate selection of the R$^4$ substitution, steric influence may be used to direct the orientation of the [3+2] cycloaddition.

Example 2

Figure 3:
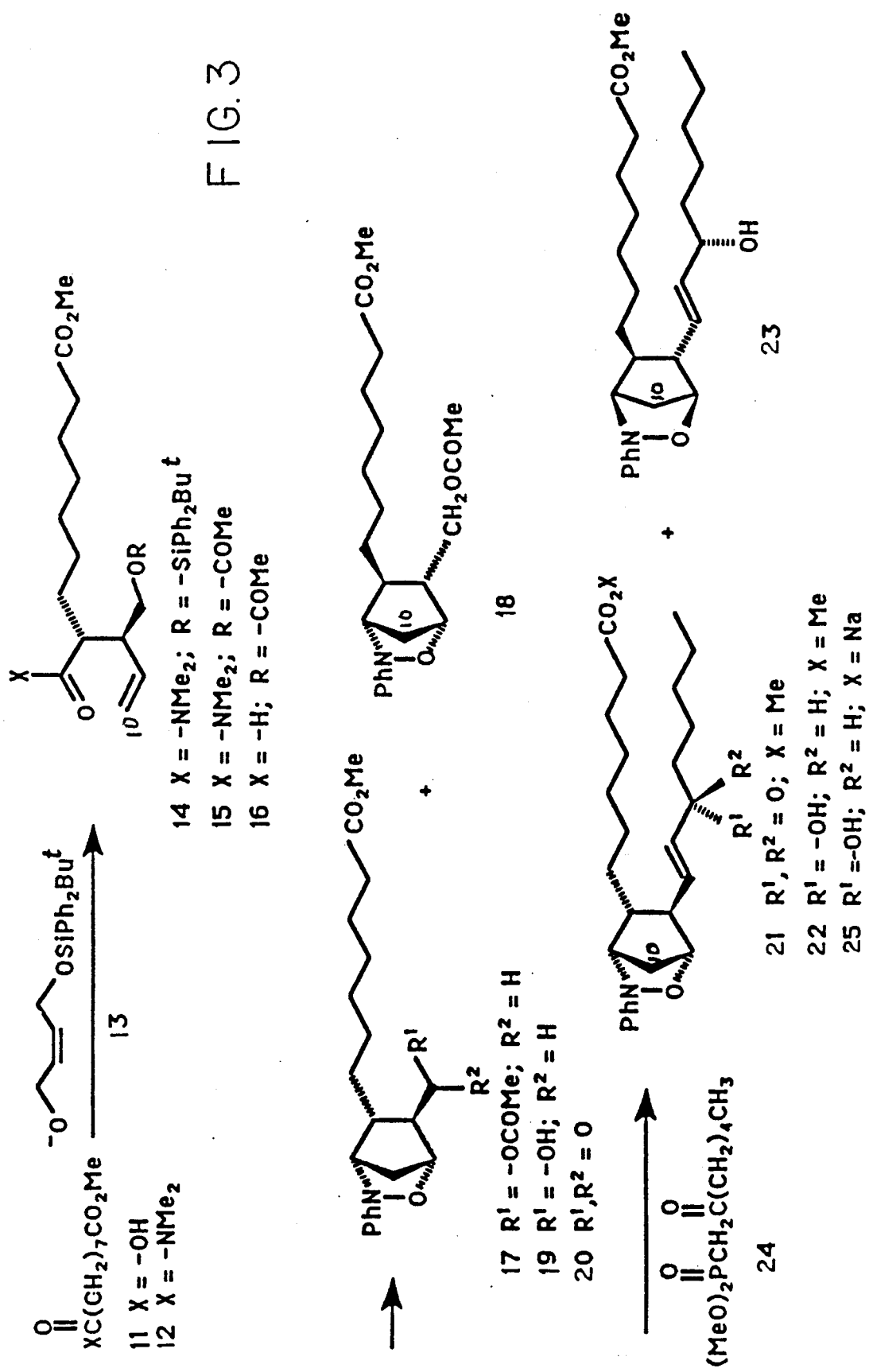

This examples makes reference to the reactions shown in FIG. 3.

PGH analogues (−)-(22), (+)-(23) and (25) were prepared beginning with azelaic acid monomethyl ester (11), a commercially available reagent. Treatment of this acid with thionyl chloride followed by aqueous dimethylamine afforded the corresponding amide (12) in 92% yield. Reaction of amide (12) with methyl triflate followed by the addition of the cis-allyl oxide (13) (generated by the addition of MeLi to the corresponding alcohol), gave the [3,3]-sigmatropic rearrangement product (14) in 69% yield after reflux. The corresponding alcohol of (13) was prepared by the reaction of cis-2-butene-1,4-diol with t-butylchlorodiphenylsilane.

The t-butyldiphenylsilyloxy group in (14) was replaced with an acetate moiety by a one-pot, two step process. Thus, treatment of (14) with tetra-n-butylammonium fluoride followed by the addition of acetic anhydride and triethylamine gave amide (15) in 98% yield. Treatment of amide (15) with methyl triflate, followed by the addition of L-selectride in situ afforded aldehyde (16) in 50% yield.

Aldehyde (16) was converted to bicyclic isoxazolidine (17) (33%) and (18) (42%) upon treatment with phenyl hydroxylamine in bromobenzene at 0° C. followed by refluxing. Isomer (18) could easily be separated from (17) by chromatography.

Treatment of (17) with methanolic KOMe gave alcohol (19) in 82% yield. This alcohol was readily oxidized to the corresponding aldehyde (20) in 93% yield by using oxalyl chloride-dimethyl sulfoxide and triethylamine. Reaction of the sodium salt of the β-keto phosphonate (24) with aldehyde (20) in dimethoxyethane afforded trans enone (21) in 92% yield.

Treatment of enone (21) with (S)-BINAL-H gave PGH analogues (−)-(22)(36% yield) and (+)-(23)(38% yield) in 86% and 78%, e.e., respectively. The % e.e. values were determined by the comparison of the NMR spectra of the (R)-β,β,β-trifluoro-αmethoxy-α-phenyl-proprinates (MTPA esters) of (−)-(22) and (+)-(23) with the MTPA esters of (+)-(22) and (+)-(23), respectively. Saponification of the methyl ester group of (−)-(22) with methanolic NaOH gave (25) in 85% yield.

A more detailed description of the foregoing preparations according to FIG. 3 follows. All numbered compound designations refer to FIG. 3.

All reactions were carried out in ovendried glassware (4 hr, 120° C.) under an atmosphere of nitrogen. Dichloromethane, bromobenzene, dimethyoxyethane, oxalyl chloride, dimethyl sulfoxide, and triethylamine were dried and distilled over CaH$_2$. Tetrahydrofuran (THF) was freshly distilled from Na/benzophenone. Analytical TLC was performed on commercially available precoated plates (silica gel GHLF) using UV light and/or 2.5% phosphomolybdic acid in ethanol with heating for visualization. Mixtures of ethyl acetate and hexanes were used as eluants. Infrared spectra (IR) were measured on a Perkin-Elmer 599B spectrophotometer. The wavenumbers reported are referenced to the polystyrene 1601 cm$^{-1}$ absorption. IR intensities are designated using the following abbreviations: s, strong; m, medium; w, weak. $^1$H NMR were obtained on a Varian CFT-20 (80 MHz) or a Varian XL-400 (400 MHz) spectrometer using chloroform-d as solvent and tetramethylsilane as an internal standard. $^1$H NMR multiplicities are recorded by using the following abbreviations: s, singlet; d, doublet; t, triplet; q, quartet; m, multiplet; dd, doublet of doublets; br s, broad singlet; J, coupling constant (hertz). High-resolution mass spectra were obtained with a VG analytical 70-S Mass spectrometer. Optical rotations were measured in a 1-dm cell on a Perkin-Elmer 141 polarimeter and c is expressed in g/100 ml. Melting points were determined on a Buchi 510K melting point apparatus and are uncorrected. Medium pressure liquid chromatography (MPLC) equipment included a metering pump (ISCO model 312) and glass columns packed with EM Reagents silica gel 60 (partial size 0.040–0.063 mm). Preparative thin layer radial chromatography was performed by a chromatotron using EM Reagents silica gel 60 PF$_{254}$. Mixtures of ethyl acetate and hexanes were used as eluting solvents.

(a) Preparation of methyl N,N-dimethylcarbamoylnonanoate (12)

A 100 ml flask fitted with a reflux condenser was charged with acid (11) (16.16 g., 79.9 mmol, 1.0 equiv) and thionyl chloride (15.50 g, 130.2 mmol, 1.6 equiv) at room temperature. The mixture was heated briefly to initiate the reaction. After the exothermic release of SO$_2$ and HCl had subsided, the flask was immersed in an oil bath and heated at 80° C. for 2 hr. The flask was fitted with a distillation apparatus and excess thionyl chloride was removed at atmospheric pressure. The residue (crude acid chloride) was then placed under vacuum (H$_2$O aspirator) for 20 min. The acid chloride was added dropwise over a 5 min period to an ice cold solution of dimethyl amine (40% in H$_2$O, 31.7 g, 281 mmol) in H$_2$O (20 ml). After another five minutes, the mixture was added to a separatory funnel and extracted 3 times with Et$_2$O. The combined Et$_2$O layers were washed successively with 10% HCl, H$_2$O, and saturated aqueous NaHCO$_3$, then dried over MgSO$_4$(s) Filtration and removal of the solvent gave a yellow liquid which was distilled at reduced pressure (bp 118–120° C., 0.05 mm Hg) to give amide (12) (15.97 g, 69.6 mmol, 87%): TLC R$_f$ 0.12 (40% EtOAc in hexanes); $^1$H NMR(CDCL$_3$, 80 MHz) δ1.14–1.79(m, 10H, (CH$_2$)$_5$), 2.17–2.43 (m, 4H, 2×CH$_2$CO), 2.94 (s, 3H, NCH$_3$), 2.99 (s, 3H, NCH$_3$), 3.66 (s, 3H, NCH$_3$), 3.66 (s, 3H, OCH$_3$); IR(neat)2937(m), 2861 (m), 1738 (s, C=O), 1645 (s, C=O), 1400(w), 1261 (m, C—O), 1200(m,C—O),

(b) Preparation of Amide (14)

A solution of amide (12) (6.85 g., 29.9 mmol, 1.0 equiv) and methyl trifluoromethanesulfonate (5.40 g., 32.9 mmol, 1.1 equiv) in $CH_2Cl_2$(35 ml) was stirred at room temperature for 16 hr. The solvent was removed by rotary evaporation (T=35° C.) and the residue was placed under high vacuum until it reached constant weight. The resulting oil was dissolved in THF (23 ml) and added dropwise over a 15 min period to an ice cold solution of the monosilylated lithium alkoxide (13). The alkoxide solution was prepared by the addition of MeLi (1.02 M in $Et_2O$, 29.3 ml, 29.9 mmol, 1.0 equiv) to the corresponding monosilylated diol (9.75 g, 29.9 mmol, 1.0 equiv) in THF (55 ml) at 0° C. The mixture was kept at 0° C. for 45 minutes after the addition of the amide salt was complete. The flask was then fitted with a distillation apparatus and the solution was distilled until the head temperature reached 60° C. (=50 ml of distillate). The flask was then fitted with a reflux condenser and the solution was refluxed for 44 hr. After the reaction mixute was cooled to room temperature, the solvent was removed by rotary evaporation and the residue was added to saturated aqueous $NaHCO_3$ and extracted 3 times with $Et_2O$. The combined ethereal layers were washed with saturated aqueous NaCl and dried over $MgSO_{4(s)}$. Filtration and removal of the solvent gave about 16 g of yellow oil which was purified by MPLC (5cm×60 cm column, 30% EtOAc in hexanes (1.7 l) followed by 40% EtOAc in hexanes (3.0 l), collected 14 mls/tube at a flow rate of 60 ml/hr). Tubes 219-303 contained pure amide 4(9.02g). Tubes 204-218 (2.70 g) contained the desired amide plus less polar impurities and was repurified by chromatotron (4mm plate, 30% EtOAc in hexanes, 1.35 g each injection) to give additional amide 14 (1.99 g). The pure amide fractions were pooled to give a colorless oil. (11.01 g, 20.5 mmol, 69%): TLC $R_f$0.39 (40% EtOAc in hexanes); $^1$H NMR ($CDCl_3$, 400 MHz) $\delta$1.06(s, 9H, $C(CH_3)_3$), 1.06-1.66(m, 10H, $(CH_2)_5$), 2.81 (t, J=7.2 Hz, 2H, $CH_2CO$), 2.36 (m, 1H,$H_{12}$), 2.92 (s, 3H, $NCH_3$), 3.05 (s, 3H, $NCH_3$), 3.10 (m, 1H, $H_8$), 3.66 (s, 3H, $OCH_3$), 3.69 (dd, J=4.8, 10.2 Hz, 1H, $H_{13}$), 3.72(dd,J=4.3,10.2 Hz, 1H, $H_{13'}$), 4.97-503 (m,1H,$H_{10}$), 5.94(m,1H,$H_{11}$), 7.34-7.67(m,10H,2ArH); IR(neat) 3073(m,=C—H), 3051(m,=C—H), 2938(s), 2861(s), 1739(s,C=O), 1643(s,C=O), 1435(m), 1268(m), 1179(m, C—O), 1121(m), 830(m), 747(s), 707(s) $cm^{-1}$, exact mass calcd for $C_{32}H_{47}NO_4Si$:537.3274; found: 537.3269.

(c) Preparation of Amide (15)

A solution of amide (14) (10.36 g, 19.3 mmol, 1.0 equiv) in THF (60 ml) was treated with solid tetra-n-butylammonium flouride trihydrate ($TBAF \cdot 3H_2O$, 7.60 G, 24.1 mmol, 1.25 equiv) at room temperature. After stirring for 3 hr, the solution was treated with triethylamine (7.80 g, 77.1 mmol, 4.0 equiv) and $Ac_2O$ (9.85 g, 96.5 mmol, 5.0 equiv) and stirred for an additional 1.5 hr. The mixture was added to saturated aqueous $NaHCO_3$ and extracted 3 times with $Et_2O$. The combined ethereal layers were washed with saturated aqueous NaCl, dried ovr $MgSO_{4(s)}$ and filtered. Removal of the solvent followed by filtration of the residue through a plug of silica gel ($Et_2O$ as eluant) gave a pale yellow oil. Purification of the oil by MPLC (2.5 cm×45 cm column, 50% EtOAc in hexanes) afforded the product (15) as a clear, colorless oil (6.46 g, 18.9 mmol, 98%): TLC $R_f$ 0.21 (40% EtOAc in hexanes); $^1$H NMR($CDCCl_3$, 400 MHz) $\delta$1.12-1.76(m,10H,$(CH_2)_5$, (2.05(s,3H,$CH_3CO$),2.29(t,J=7.6 Hz, 2H, $CH_2CO$),2.62(m,1H,$H_{12}$), 2.90(m,1H,$H_8$), 2.95(s,2H,$NCH_3$) 3.05(s,3H,$NCH_3$), 3.66(s,3H,$OCH_3$), 4.09(dd, J=5.6, 9.8 Hz, 1H, $H_{13}$), 4.15 (dd, J=7.2, 9.8 Hz,1H,$H_{13'}$), 5.05-5.12(m,2H,$H_{10}$), 6.82(m,1H,$H_{11}$); IR(neat) 3082(w,=C-H), 2942(m), 2868(m),1739(s,C=O), 1642(s,C=O), 1441(m), 1403(m), 1370(m), 1238(s,C—O), 1175(m,C—O), 1041(m), 939(w)$cm^{-1}$, exact mass calcd for $C_{18}H_{31}NO_5$:341.2202; found:341.2187.

(d) Preparation of Aldehyde (16)

A solution of amide (15) (1.440 g, 4.22 mmol, 1.0 equiv) and MeOTf (3.48 g. 21.2 mmol, 5.0 equiv) in $CH_2Cl_2$(10ml) was stirred at room temperature for 4 days. The solvent was removed by rotary evaporation (T=35° C.) and the residue, a dark oil, was placed under high vacuum until it reached constant weight. A solution of the residue in THF (925 ml) was cooled to −78° C. and treated with lithium tri-sec-butyl-borohydride available as L-Selectride (1.0 M in THF, 4.64 ml, 4.64 mmol, 1.1 equiv) over a 7 min period. The solution changed from clear black to pale yellow during the addition. After 1 hr at −78° C., the mixture was immersed in an ice bath for 1 min, then quenched with 25 ml of saturated aqueous $NH_4Cl$. The mixture was diluted with a small amount of $H_2O$ and extracted 3 times with $Et_2O$. The combined ethereal layrs were washed with saturated aqueous NaCl, dried over $MgSO_{4(s)}$ and filtered. Removal of the solvent afforded a yellow liquid which was chromagraphed by chromototron (4 mm plate, 20% EtOAc in hexanes). Impure aldehyde (16) was obtained as a pale yellow liquid (975 mg) along with pure recovered starting material (266 mg). Final purification of the impure mixture by chromatotron (4 mm plate, 15% EtOAc in hexanes) afforded pure aldehyde 6 (626 mg, 2.1 mmol, 50%, (61% based on recovered starting material TLC Rf 0.57 (40% EtOAc in hexanes); $^1$H NMR ($CDCl_3$, 400 MHz) $\delta$1.22-1.75(m, 10H, $(CH_2)_5$), 2.04 (s, 3H, $CH_3CO$), 2.30 (t, J=7.4 Hz, 2H, $CH_2CO$), 2.38(m, 1H,$H_8$), 2.79 (m,1H,$H_{12}$),3.67(s,3H,$OCH_3$), 4.10 (dd, J=7.2, 10.8 Hz, 1H, $H_{13}$), 4.16 (dd,J=6.4,10.8 Hz, 1H, $H_{13'}$), 5.12-5.22(m,2H,$H_{10}$), 5.73(m,1H,$H_{11}$), 9.63(d,J=2.4 Hz,1H,CHO); IR(neat) 3083(w,=C—H), 2929(m), 1237(s,C—O), 1175(s,C-O), 1039(m,C-O), 932(m), 736(w)$cm^{-1}$; exact mass (M—H)$^+$calcd for $C_{16}H_{25}O_5$:297.1702; found: 297.1700.

(e) Preparation of Isoxazolidines (17) and (18)

A solution of phenyl hydroxylamine (172 mg, 1.58 mmol, 1.07 equiv) in bromobenzene (5.0 ml) and $Et_2O$(0.5 ml) was added over a 2 hr period to a stirred suspension of freshly purified aldehyde (16) (441 mg, 1.48 mmol, 1.0 equiv), 5A molecular sieves (5.1 g), and bromobenzene (7.0 ml) while the reaction was maintained at −7° C. The reaction mixture was maintained at −7° C. for an additional 3 hours, then diluted with 15 ml of cold (−7° C.) bromobenzene. The reaction flask was then immersed in an oil bath pre-heated to 170° C. After heating for 8 min, the mixture was quickly cooled to room temperature and filtered through a pad of Celite. The solvent was removed by rotary evaporation and the residue was filtered through silica gel ($Et_2O$ as eluant) to give an orange-red oil. Purification of the oil by chromatotron (2 mm plate, 15% EtOAc in hexanes) gave a mixture of isoxazolidines (17) and (18). Separation of this crude mixture again by chromatotron (2 mm plate, 10% EtOAc in hexanes) gave isoxazolidine (17) (192 mg, 0.49 mmol, 33%) and isoxazolidine (18) (241 mg, 0.62 mmol, 42%) as oils.

For (17): TLC $R_f$ 0.28 (20% EtOAc in hexanes); $^1$H NMR (CDCl$_3$, 400 MHz) δ1.27-1.70 (m, 10H, (CH$_2$)$_5$), 1.65(d,J=10.8 Hz, H$_{10a}$), 1.77-1.87(m,2H,H$_8$ and H$_{10s}$), 1.96 (m,1H,H$_{12}$), 2.08 (s,3H,CH$_3$CO), 2.32(t,J=7.4 Hz, 2H, CH$_2$CO), 3.67 (S,3H,OCH$_3$), 3.79(dd,J=9.2,11.2 Hz,1H, H$_{13}$),3.98(dd, J=4.8,1.2 Hz, 1H, H$_{13'}$), 3.98 (br s, 1H, H$_9$), 4.56(br s, 1H, H$_{11}$), 6.92-7.28(m,5H,ArH); IR(neat) 3062 (w,=C—H), 2925(s),2853(s),1732(s,C=O), 1598(m,C=C),1487(m,C=C),1437(m),1368(m),1231(s,-C—O), 1169(s,C—O), 1029(m), 978(m), 935(m), 784(w), 761(m), 701(s,—=C—H) cm$^{-1}$; exact mass calcd for C$_{22}$H$_{31}$NO$_5$:389.2202; found: 389.2207.

For (18): TLC $R_f$ 0.23 (20% EtOAc in hexanes); $^1$H NMR (CDCl$_3$, 400 MHz) δ1.29-1.70 (m, 11H, (CH$_2$)$_5$ and H$_8$), 1.62-1.68 (m,2H,H$_{10a}$ and H$_{12}$), 1.93 (m,1H,H$_{10s}$),2.06(s,3H,CH$_3$CO), 2.32(t, J=7.4 Hz, 2H, CH$_2$CO), 3.67(s,3H,OCH$_3$), 3.85(br s, 1H,H$_9$), 4.18 (dd,J=9.2,10.8 Hz, 1H, H$_{13}$), 4.26 (dd,J=5.8,10.8 Hz,1H,H$_{13'}$), 4.63 (br s,1H,H$_{11}$), 6.92-7.28(m,5H,ArH); IR (neat) 3065(w,=C—H),2932(s), 2859(s), 1731(s,C=O),1599(m,C=C), 1492(m,C=C), 1443(m), 1370(m), 1239(s,C—O),1174(s,C—O), 1031(m), 980(m), 943(w), 909(w), 767(m), 703(s,=C—H) cm$^{-1}$; exact mass calcd for C$_{22}$H$_{31}$NO$_5$:389.2202; found: 389.2205.

(f) Preparation of Alcohol (19)

A mixture of acetate (17) (155 mg, 0.40 mmol, 1.0 equiv), KOMe (Alpha, 5mg, 0.09 mmol, 0.23 equiv) and MeOH (10 ml) was stirred at room temperature for 2 hr. The solution was then added to saturated aqueous NaHCO$_3$ and extracted 3 times with Et$_2$O. The combined Et$_2$O extracts were washed with saturated aqueous NaCl and dried over CaSO$_{4(s)}$. Filtration and removal of the solvents afforded an oil which was purified by chromatotron (2 mm plate, 30% EtOAc in hexanes). The alcohol (19) was obtained as a colorless oil (133mg, 0.33 mmol, 82%) which solidified upon standing in the freezer: mp 58.0-60.0° C.; TLC $R_f$ 0.26 (40% EtOAc in hexanes); $^1$H NMR(CDCl$_3$, 400 MHz) δ1.33-1.66(m,11H,(CH$_2$)$_5$ and H$_8$), 1.67 (d, J=10.4Hz, 1H, H$_{10a}$), 1.77-1.88 (m,3H,H$_{10s}$,H$_{12}$ and OH), 2.32(t,J=7.6Hz,2H,CH$_2$CO), 3.37(m) 1H,H$_{13}$, 3.58(m,1H,H$_{13'}$), 3.67(s,3H,OCH$_3$], 3.98,(br s,1H,H$_9$), 4.65(br s, 1H, H$_{11}$), 6.91-7.28(m,5H,ArH); IR(neat)3441(s,O—H), 3067(w,=C—H),2930(s), 2857(s), 1731 (s,C=O), 1598 (m,C=C), 1489 (m,C=C),1444(m), 1256(s,C—O), 1171(s,C—O), 1022(m,C—O), 935(m), 764(m), 703(s,=C—H)cm$^{-1}$; exact mass calcd for C$_{20}$H$_{29}$NO$_4$:347.2098; found:347.2131.

(g) Preparation of Aldehyde (20)

A 15-ml flask was charged with CH$_2$Cl$_2$ (1.5 ml) and oxalyl chloride (48.0mg, 0.38 mmol, 1.23 equiv) and cooled to −55° C. A solution of DMSO (66mg, 0.85 mmol, 2.74 equiv) in CH$_2$Cl$_2$(0.2ml) was added dropwise to the mixture over a 4 min period. The alcohol (19) (109 mg, 0.31 mmol, 1.0 equiv) in CH$_2$Cl$_2$ (0.5 ml) was then added dropwise over a 5 min period. The solution gradually turned a cloudy pink color. After 15 min, the mixture was treated with triethylamine, (0.24 ml), stirred for an additional 5 min at −55° C., and then the solution was warmed gradually to room temperature. The solution changed from pastel pink to pale tan during the addition. Methylene chloride was added to the reaction mixture and the organic layer was washed with H$_2$O. The aqueous layer was back-extracted with CH$_2$Cl$_2$ and the combined organic layers were washed with saturated aqueous NaCl and dried over MgSO$_{4(s)}$. Filtration and removal of the solvent followed by purification by chromatotron (1mm plate, 20% ETOAc in hexanes) gave aldehyde (20) as an oil (100 mg, 0.29 mmol, 93%):TLC $R_f$ 0.25 (20% ETOAC in hexanes); $^1$H NMR (CDCl$_3$, 400 MHz) δ1.32-1.73 (m,11H,(CH$_2$)$_5$ and H$_{10a}$), 1.89 (m,1H,H$_{10s}$) 2.31 (t,J=7.6Hz,2H,CH$_2$CO), 2.35 (m,1H,H$_8$), 2.68(d,J=5.6Hz,1H,H$_{12}$), 3.67(s,3H,OCH$_3$), 4.06(br s,1H,H$_9$), 4.89 (br s,1H,H$_{11}$), 6.94-7.29 (m,5H,ArH), 9.73(d,J=0.7Hz,1H,CHO); IR (neat) 2938(s),2859(m), 2730 (w,O=C—H), 1724(s,C=O), 1600(m,C=C), 1489(m), 1458(m), 1443(m), 1255(m,C—O), 1177 (m,C—O), 1101 (m,C—O), 762(m),702(s,=C=H)cm$^{-1}$; exact mass calcd for C$_{20}$H$_{27}$NO$_4$:345.1942; found:345.1932.

(h) Preparation of α, β-Unsaturated ketone (21)

To a suspension of NaH (60% in mineral oil, 12.6 mg, 0.315 mmol, 1.12 equiv) in dimethoxyethane (3.5 ml) was added dropwise dimethyl (2-oxoheptyl) phosphonate (77.0 mg, 0.347 mmol, 1.23 equiv). After one hr, the mixture was cooled to 0° C. and treated with a solution of aldehyde (20) (97.4 mg, 0.282 mmol, 1.0 equiv) in dimethoxyethane (0.5 ml) over a 3 min period. After 1 hr at 0° C., the reaction mixture was partitioned between Et$_2$O and saturated aqueous NaCl and the aqueous layer was extracted 3 times with Et$_2$O. The combined ethereal layers were dried over CaSO$_{4(s)}$, filtered, and evaporated. The residue was filtered through a plug of silica gel (Et$_2$O as eluant) and purified by chromatotron (2mm plate, 10% EtOAc in hexanes). Pure enone (21) was obtained as a near colorless oil(114.6 mg, 0.26 mmol, 92%):TLC $R_f$ 0.42 (20% EtOAc in hexanes); $^1$H NMR (CDCl$_3$, 400 MHz) δ0.90 (t,J=7.0 Hz, 3H, CH$_3$), 1.23-1.72(m,14H,-CH$_2$-), 1.70 (d,J=10.8 Hz,1H,H$_{10a}$), 1.85 (m,2H,CH$_2$), 1.90(m,1H,H$_{10s}$), 2.31(t,J=7.2Hz,2H, CH$_2$CO$_2$Me), 2.43 (m,1H,H$_{12}$), 2.53 (t,J=7.2 Hz, 2H,H$_{16}$), 3.66(s,3H, OCH$_3$), 4.04(br s,1H,H$_9$), 4.51(br s,1H,H$_{11}$), 6.14 (d,J=15.6Hz,1H,H$_{14}$), 6.59 (dd,J=8.4, 15.6Hz,H$_{13}$), 6.93-7.28(m,5H,ArH);IR(neat)3058 (w,=C—H), 931(s),2860(s),1742(s,C=O),1695(m),1673(s,C=O conj.), 1624 (s,C=C), 1589 (s,C=C), 1489(s,C=C), 364(m), 1249 (s,C—O), 1172 (s,C—O), 982(m), 929(m), 765(m), 703 (s,=C—H) cm$^{-1}$; exact mass calcd for C$_{27}$H$_{39}$NO$_4$; 441.2879; found:441.2888.

(i) Preparation of PGH anlogs(−)-(22) and (+)-(23)

To a dry 15 ml flask was added a solution of LiAlH$_4$ in THF(1.17M, 695 μl, 1, 0.81 μmol, 3.2 equiv). A solution of EtOH in THF (0.99M, 820 μl, 0.81 μmol, 3.2 equiv) was then added at room temperature over a period of 7 minutes. Subsequently, a solution of (S)-(−)- 1,1'-bi-2-naphthol (232.6 mg, 0.81 mmol, 3,2 equiv) in THF (2.0 ml) was added dropwise over a 10 min period, resulting in a milky white near-solution which contained no precipitate. After stirring at room temperature for 30 min, the mixture was cooled to −100 ° C. using a liquid N$_2$/methanol bath. Enone (21) (112.1 mg, 0.254 mmol, 1.0 equiv) in THF (1.5 ml) was added to the solution over an 8 min period. The resulting mixture was stirred at −100 °C. for 2 hr then at −78° C. for an additional 2 hr. After quenching with 700 μl of methanol, the solution was warmed to room temperature and partitioned between Et$_2$O and saturated acqueous NaHHCO$_3$. The acqueous layer was extracted 3 times with Et$_2$O and the combined ethereal extracts were washed with saturated acqueous NaCl and drived over CaSO$_{4(s)}$. Filtration and removal of the solvent gave a yellow oil which was triturated with 20% EtOAc in hexanes to remove most of the recovered binaphthol. The solvent of the supernatant was removed and the residue was placed on the chromatotron (2mm plate, 20% EtOAc in hexanes) to obtain a mixture of isoxazolidines (−)-12 and (+)-13. The mixture was separated by HPLC (Magnum 9 Partisil 10, 9.4 mm×25 cm columnm, 20% Et$_2$O in hexanes as eluant, 3.0 ml,min flow rate, t$_R$ of(−)-(22) 102 min, t$_R$ of (+)-23 84 min) to give isoxazolidine (−)-22 (40.8 mg, 0.092 mmol, 36%) and isoxazolidine (+)-23 (42.8 mg, 0.096 mmol, 38%) in > 99% diastereomeric purity.

For (−)-(22):TLC R$_f$0.14 (20% EtOAc in hexanes); $^1$H NMR (CDCl$_3$, 400 MHz) δ0.90 (t,J=6.6Hz,3H,CH$_3$), 126–1.79 (m,20H,(CH$_2$)$_9$ and H$_8$ and H$_{10a}$), 1.83 (m,1H,H$_{10s}$), 2.27–2.33 (m,3H CH$_2$CO and H$_{12}$), 3.67 (s,3H,OCH$_3$),3.99 (br s,1H, H$_9$), 4.05(m,1H,H$_{15}$), 4.42 (br s,1H,H$_{11}$), 5.45 (dd,J=7.4,15.6Hz,1H,H$_{13}$), 5.54 (dd,J=6.4,5.6Hz,1H, H$_{14}$), 6.92–7.28 (m,5H,ArH); IR (neat) 3391 (s,O—H), 922(s), 2855(s), 1724(s,C=O), 1594 (m,C=C), 248(s,C—O), 1169(s,C—O), 1024(m,C—O), 969(m), 923(m), 761(m), 701(s,=C—H) cm$^{-1}$; exact mass calcd for C$_{27}$H$_{41}$NO$_4$:443.3036; found;443.3042; [α]D$^{22.5}$−109.3(c 0.35, THF), 86% e.e. based on $^1$H NMR (CDC;$_3$, 400 MHz) analysis of the (R)-β, β, β-trifluoro-α-methoxy-αphenylpropionates (MTPA esters).

For (+)-(23):mp 56.0–58.0 °C.;TLC R$_f$0.15 (20% EtOAc in hexanes);$^1$H NMR (CDCl$_3$, 400 MHz) δ0.91(t,J=6.6 Hz, 3H, CH$_3$), 1.25–1.79 (m, 20H, (CH$_2$)$_9$ and H$_8$ and H$_{10a}$), 1.82 (m, 1H,H$_{10s}$), 2.27–2.33 (m,3H,CH$_2$CO and H$_{12}$), 3.67 (s,3H, OCH$_3$ 4.00 (br s, 1H, H$_9$), 4.06 (m,1H,H$_{15}$), 4.40 (br s, 1H,H$_{11}$), 5.46 (dd,J=7.4, 15.6 Hz,1H,H$_{13}$), 5.54 (dd,J=6.4,15.6 Hz,1H,H$_{14}$), 6.92–7.27 (m,5H,ArH); IR(CCl$_4$) 3619 (w, free O—H), 3498 (m,O—H), 2930(s), 2858(s), 1737(s,C=), 1598 (m,C=C), 1489 (m,C=C), 1441(m), 1251(m,C—O), 1160 (s,C—O), 1021 (m,C—O), 972(m),927(m),700(s,=C—H)cm$^{-1}$; exact mass calcd for C$_{27}$H$_{41}$NO$_4$:443.3036; found:443.3046-;[α]$_D^{22.5}$+116.9(c 0.44,THF), 78% e.e. based on $^1$H NMR (CDCl$_3$, 400 MHz) analysis of the MTPA esters.

(j) Preparation of Racemic PGH analogs ((±)-22 and ((±)23)

To a solution of enone (21) (14.8 mg, 33.5 μmol, 1.0 equiv) in THF (500 μl) at −78 °C. was added L-selectride (1.0M in THF, 50 μmol, 1.5 equiv). The reaction was stirred at −78 °C. for 45 min, then quenched with saturated acqueous NH$_4$Cl. The mixture was partitioned between Et$_2$O and H$_2$O and extracted 2 times with Et$_2$O. The combined ethereal layers were washed with saturated acqueous NaCl and dired over CaSO$_{4(s)}$. Filtration and removal of the solvent, followed by purification of the residue by HPLC (Magnum 9 Partisil 10, 9.4 mm x 25 cm column, 20% Et$_2$O in hexanes as eluant, 3.0 ml/min flow rate, t$_R$ of (±)-(22) 102 min, t$_R$ of (±)-23 84min) gave (±)-(22) (5.4 mg, 12.2 μmol, 36% and 12.8 μmol, 38%).

(k) Derivatization of Alcohols with the MTPA Acid Chloride

Isoxazolidines (22) and (23) were derivitized in the following manner: The isoxazolidine (6mg, 13.5 μmol, 1.0 equiv) was dissolved in pyridine (200 μl) and CCl$_4$ (200μl0. α-methoxy-α-(trifluoromethyl) phenylacetyl chloride (12 mg, 48 μmol, 3.5 equiv, prepared from (R)-(+)-α-methoxy-α-(trifluoromethyl)phenylacetic acid) was added to the solution and the resulting mixture was stirred at room temperature for 1.5 hr. The solution was then diluted with Et$_2$SO$_{4(s)}$, filtered, and the solution was removed. The residue was checked by NMR after filtration through silica gel.

$^1$H NMR (400 MHz, CDCl$_3$) analysis of the MTPA ester of (±)-(22) showed two sets of peaks at δ4.35 (51%) and & 4.38 (49%) corresponding to the bridgehead H$_{11}$ protons. Two distinct sets of peaks were also observed at δ3.54 (52%) and δ3.56 (45%) corresponding to the methoxy groups of the MTPA esters. $^1$H NMR (400 MHz, CDCl$_3$) analysis of the MTPA ester of (±)-(23) showed two sets of peaks at δ 4.35 (50%) and δ 4.39 (50%) corresponding to the bridgehead H$_{11}$ protons. Two distinct sets of peaks were also observed at δ3.53 and δ3.57 (49%) corresponding to the methoxy groups of the MTPA esters.

The present enantiomeric excess (% e.e.) of (−)-(22) was estimated to be 86% based on $^1$H NMR (400 MHz, CDCl$_3$) analysis of the MTPA esters. The NMR spectrum showed two sets of peaks at δ4.35 (93%) and & 4.38(7%) corresponding to the bridgehead H$_{11}$ protons. Peaks at δ3.54 (7%) and δ3.56 (93%) correponding to the methoxy groups of the MTPA esters were also observed. The percent enantiomeric excess (% e.e) of (+)-(23) was estimated to be 78% based on $^1$H NMR (400 MHz, CDCl$_3$) analysis of the MTPA esters. The NMR spectrum showed two sets of peaks at δ4.35 (89%) and δ4.39 (11%) corresponding to the bridgehead H$_{11}$ protons. Peaks at δ3.53 (12%) and δ3.57 (88%) corresponding to the methoxy groups of the MTPA esters were also observed.

It is contemplated that the prostanoids of the invention, e.g., (−)-(22), (+)-(23) and (25), will have the uses or biological activities of known prostaglandins. This includes, for example, inhibition of TX, TXA$_2$ and PGI$_2$ synthetases; causing aggregation of human platelets and contraction of isolated rabbit aorta, etc. The present prostanoids, may, therefore, be used in the customary fashion of the prostaglandins. As noted earlier, the PGH analogues may also be used as intermediates in the preparation of other types of prostaglandins, e.g., PGF or the like.

It will be appreciated that the foregoing description of the invention is given only for illustrative purposes and various modifications will be evident to those in the art. A specific feature of the invention which should be mentioned in this regard is the selective reduction of the amide (15) to the corresponding aldehyde (16) as illustrated in FIG. 3. This illustrates a further unique aspect of the invention wherein the direct reduction of an amide group (X is —N alkyl such as—NMe$_2$) to an aldehyde group is accomplished with a compound which includes an ester group. Normally it is not possible to accomplish such direct reduction of an amide group to an aldehyde group in the presence of an ester group because the ester group reacts first. However, the invention contemplates activating the amide with methyl triflate or the like followed by treatment with a lithium alkylborohydride, e.g. lithium tri-sec-butylborohydride to reduce the amide without affecting the ester group. This is illustrated in Example 2(d).

While specific intermediates have been referred to in the foregoing, the invention contemplates general categories of such intermediates as well as final products as will be evident. For instance, compounds (17) and (18) as shown in FIG. 3 are representations of compounds according to the invention having the formula

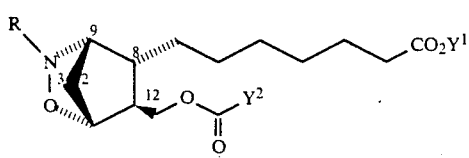

or the formula

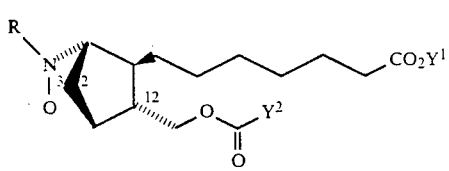

where R is hydrogen, or optionally substituted alkyl, aryl or aralkyl as defined above; $Y^1$ is hydrogen, alkali metal, alkyl, aryl or aralkyl preferably alkyl of up to 8 carbons, phenyl or benzyl; and $Y^2$ is alkyl, preferably alkyl of up to 8 carbon atoms. The scope of the invention is defined in the following claims wherein:

We claim:

1. A nitrone-alkene of the formula:

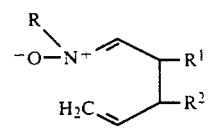

where R is phenyl and $R^1$ and $R^2$ each represent the atoms necessary to complete prostaglandin 8- and 12- side chains or fragments thereof, said $R^1$ being selected from the group consisting of

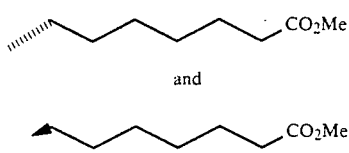

and said $R^2$ being selected from the group consisting of

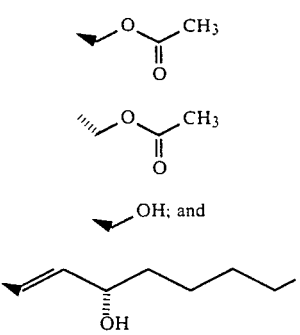

* * * * *